(12) United States Patent
Jones et al.

(10) Patent No.: US 7,393,883 B2
(45) Date of Patent: Jul. 1, 2008

(54) FILLER FOR DENTAL COMPOSITE MATERIALS

(75) Inventors: Derek W. Jones, Halifax (CA); Amin S. Rizkalla, Halifax (CA); Gordon C. Hall, Lower Sackville (CA)

(73) Assignee: New Age Biomaterials, Inc., Halifax, Nova Scotia ( * ) Notice: Subject to any disclaimer, the term of this patent is extended or adjusted under 35 U.S.C. 154(b) by 550 days.

(21) Appl. No.: 10/844,633

(22) Filed: May 13, 2004

(65) Prior Publication Data

US 2005/0256222 A1 Nov. 17, 2005

Related U.S. Application Data

(63) Continuation of application No. 10/192,876, filed on Jul. 3, 2002, now abandoned.

(51) Int. Cl.
 *A61K 6/08* (2006.01)
 *A61K 6/083* (2006.01)
 *A61C 5/00* (2006.01)

(52) U.S. Cl. ............... 523/116; 523/115; 523/118; 433/228.1

(58) Field of Classification Search .......... 523/116; 433/228.1
See application file for complete search history.

(56) References Cited

U.S. PATENT DOCUMENTS

| | | | |
|---|---|---|---|
| 3,066,112 A | 11/1962 | Bowen | |
| 3,230,184 A * | 1/1966 | Alford | ......... 523/219 |
| 3,452,437 A | 7/1969 | Chang | |
| 3,629,187 A | 12/1971 | Waller | |
| 3,709,866 A | 1/1973 | Waller | |
| 3,792,531 A | 2/1974 | Rossi | |
| 3,801,344 A | 4/1974 | Dietz | |
| 3,808,170 A | 4/1974 | Rogers | |
| 3,826,778 A | 7/1974 | Dietz | |
| 3,911,581 A | 10/1975 | Dietz | |
| 3,926,906 A | 12/1975 | Lee, II et al. | |
| 3,959,212 A | 5/1976 | Rockett et al. | |
| 3,973,972 A | 8/1976 | Muller | |
| 3,975,203 A | 8/1976 | Dietz | |
| 4,017,454 A | 4/1977 | Muller | |
| 4,032,505 A | 6/1977 | Chasar | |
| 4,215,033 A | 7/1980 | Bowen | |
| 4,374,044 A | 2/1983 | Schaefer et al. | |
| 4,447,565 A * | 5/1984 | Lula et al. | ......... 523/219 |
| 4,485,192 A * | 11/1984 | Gibbs et al. | ......... 521/54 |
| 4,491,453 A | 1/1985 | Koblitz et al. | |
| 4,514,174 A | 4/1985 | Dougherty et al. | |
| 4,674,980 A | 6/1987 | Ibsen et al. | |
| 4,681,718 A * | 7/1987 | Oldham | ......... 264/102 |
| 4,696,955 A | 9/1987 | Kuhlmann | |
| 4,818,581 A | 4/1989 | Katoh et al. | |
| 4,879,324 A | 11/1989 | Lausberg et al. | |
| 4,917,857 A * | 4/1990 | Jaeckel et al. | ......... 419/9 |
| 5,266,609 A | 11/1993 | Hall et al. | |
| 5,310,592 A * | 5/1994 | Baker et al. | ......... 428/117 |
| 5,338,773 A | 8/1994 | Lu et al. | |
| 5,710,194 A | 1/1998 | Hammesfahr et al. | |

FOREIGN PATENT DOCUMENTS

| | | |
|---|---|---|
| FR | 2702649 | 9/1994 |
| GB | 2291053 | 1/1996 |
| JP | 62-96537 | 10/1985 |
| WO | WO 96/26237 | 8/1996 |

* cited by examiner

*Primary Examiner*—Tae H Yoon
(74) *Attorney, Agent, or Firm*—McNees Wallace & Nurick LLC

(57) ABSTRACT

Ceramic filler compositions of customized shapes (FIGS. 1-30) according to the present invention, includes ceramic and glass-ceramic particles having a customized shape which provides mechanical locking within a resin matrix giving significantly improved fracture toughness performance for a resin/glass or ceramic composite system. The material has particular application as a tooth filling material with significantly improved wear resistance. The wide range of unique-shaped filler particles are produced using wet chemistry methods according to the invention of preparing the ceramic particles for use in a resin matrix composite material. Such composite materials have a very wide application, especially as a dental composite filling material for restoring a tooth.

17 Claims, 5 Drawing Sheets

FILLER FOR DENTAL COMPOSITE MATERIALS

CROSS-REFERENCE TO RELATED APPLICATIONS

This application is a continuation of U.S. Utility application Ser. No. 10/192,876, filed on Jul. 3, 2002, abandoned, which claims the benefit of U.S. Utility application Ser. No. 09/432,486, filed on Nov. 1, 1999, abandoned, which claims the benefit of U.S. Provisional Application Ser. No. 60/106,806, which was filed on Nov. 3, 1998, the disclosures of which are incorporated as if fully rewritten herein.

FIELD OF INVENTION

The present invention relates to dental products and processes and more particularly, to the fabrication of ceramic particulate materials. More particularly, the invention relates to dental filling materials formed from a resin matrix and a ceramic or glass filler in the form of a composite restorative material. More particularly, the invention relates to the production of specific shapes of ceramic particulate material ranging in size from sub-micron to about 50 µm, but preferably with a mean size of about 7 µm.

BACKGROUND OF THE INVENTION

This invention deals with development of an improved resin glass or ceramic composite system which has wide application and may be used for dental restorative filling materials for teeth and biomedical bone cement. It will be appreciated by one skilled in the art that modern 'dental composite' materials are a blend of glass and/or ceramic particles dispersed in a polymerizable synthetic organic resin. The polymer materials are blended together with the finely divided inorganic material such as a barium aluminosilicate or zirconium silicate glass or other glass ceramic compositions having an effective amount of radiopacifying agent that renders the resultant glass radiopaque to X-rays. Such dental restorative composite materials comprised of a blend of liquid polymerizable organic binder and a solid inorganic filler are known to the prior art. Such compositions are described in general terms for example in U.S. Pat. No. 3,066,112. The full potential application in dentistry of glass and glass/ceramic/resin composite biomaterials has not yet been achieved because the current composite materials cannot completely withstand the aggressive environment of the oral cavity. Major shortcomings are low fracture toughness and the inability of the composite materials to resist abrasion and wear in the mouth.

The dental restorative composite materials using the improved filler particles of this invention may be prepared according to known methods of the prior art such as employed in U.S. Pat. No. 3,066,112 which is hereby incorporated by reference for such disclosure. The improved composite restorative system having a tooth-like colour can be used to replace the conventional amalgam or gold dental fillings. Materials such as amalgam suffer from uncertainty as to the biological effect of the introduction of mercury into the oral cavity over long periods of time. In addition the metallic hue of amalgam restorations is not aesthetic.

Currently dental composite systems suffer from lack of sufficient adhesion being established between the inorganic (glass or ceramic) filler and the resin matrix. The modulus of elasticity of a composite material will show the effectiveness of the stress/strain transfer from matrix to the filler particles. The modulus of elasticity and Poisson's ratio of dental restorative materials are also regarded as important fundamental properties, because a material with a low elastic modulus will more readily elastically deform under a given masticatory functional force. Excessive elastic deformation of the restorative material under functional stress may result in catastrophic fracture of surrounding brittle tooth enamel structure, or alternatively increased microleakage may result. The increased use of polymer/glass composite systems as posterior restoratives (in back 'molar' grinding teeth) which are subjected to much higher levels of force than anterior restorations, might suggest the use of materials with a higher modulus of elasticity and fracture toughness in order to minimize the risk of cusp fractures. A dental restorative composite material with a higher modulus of elasticity and fracture toughness will be able to provide support at the interface with tooth enamel to protect the enamel rods at the margin from fracturing. Excessive wear of the restoration due to loss of filler particles (pull-out) followed by easier wearing away of the softer resin matrix is another problem in such situations.

A major limitation of the current dental composite materials is the relatively low fracture toughness. Fracture toughness is the energy absorbed by the material in resisting crack propagation. Dental restorative composite materials exhibiting higher fracture toughness values will have a better resistance to fracture and functional wear.

OBJECTS OF THE INVENTION

None of the composites heretofore known in the art disclose or suggest the novel method for producing the unique filler particles for composites as in the present invention. An object of this invention therefore, is to provide a ceramic filler for a composite resin material exhibiting a capability to mechanically lock into the resin matrix but at the same time not produce the high stress concentration around the filler that can occur with an irregular shaped filler. The incorporation of the unique shaped particles will significantly increase the fracture toughness and wear resistance of the composite.

These and other objects of the invention, which shall become apparent from the description to follow, are achieved by the invention as hereinafter described and claimed.

SUMMARY OF THE INVENTION

In general, the present invention provides a method to synthesize ceramic filler components with a specific shape, such that it will allow mechanical interlocking into the organic resin matrix. The incorporation into a resin composite of from about 5 to about 35% by weight of these unique shaped particles together with conventional glass filler will result in a significantly higher fracture toughness and improved wear resistance. Specific shaped particles can also be incorporated to control consistency to produce a flowable or packable composite material. In addition, spherical particles of silica, alumina or zirconium, titanium, barium or strontium silicate synthesized by wet chemical methods can also be blended together with the specific shaped type of ceramic filler to improve packing density. The invention provides unique filler particle for use in dental composites.

BRIEF DESCRIPTION OF THE ILLUSTRATIONS

Figure 5:
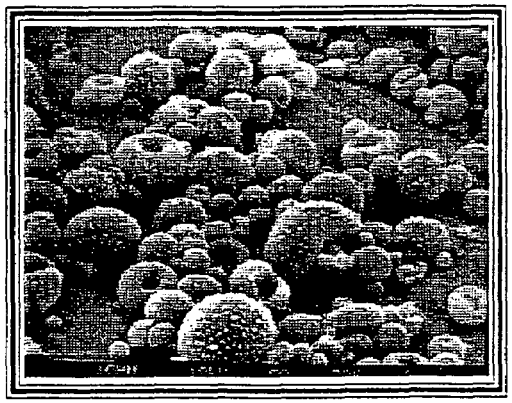
Figure 6:
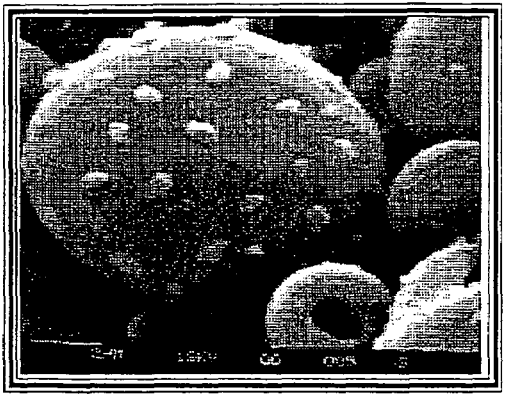
Figure 7:
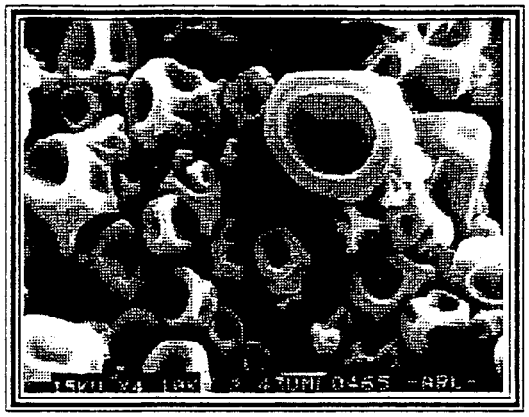
Figure 8:
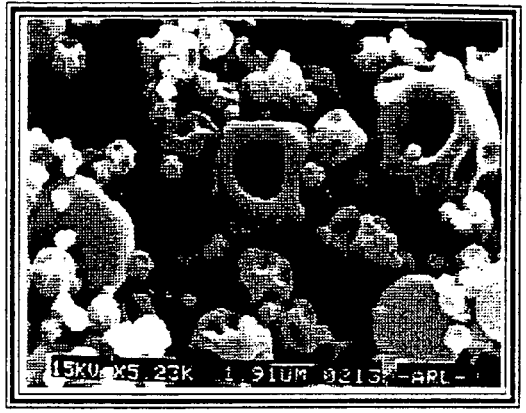
Figure 9:
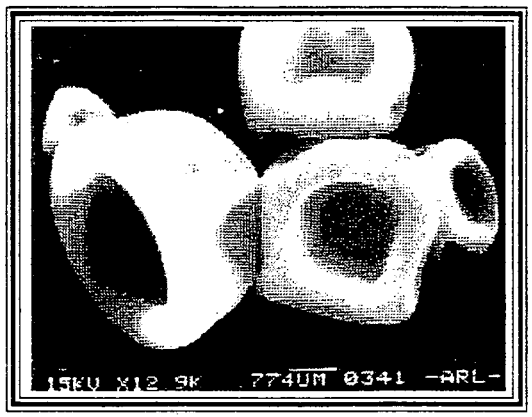
Figure 10:
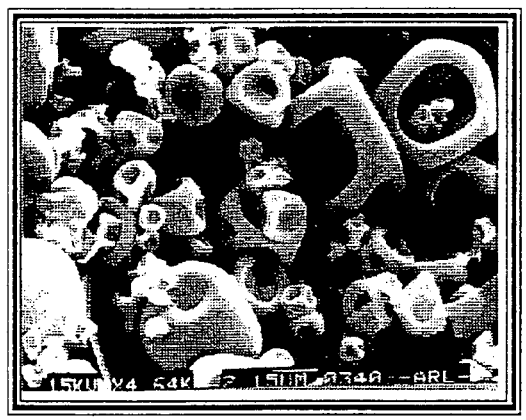
Figure 11:
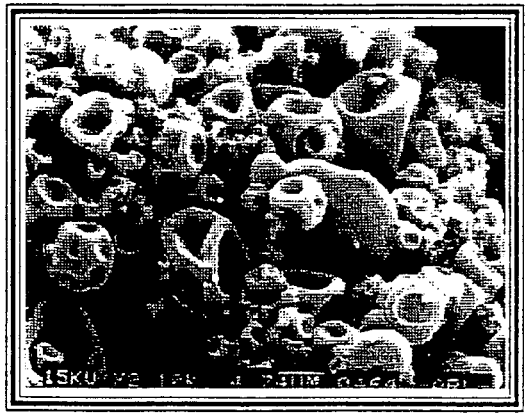
Figure 12:
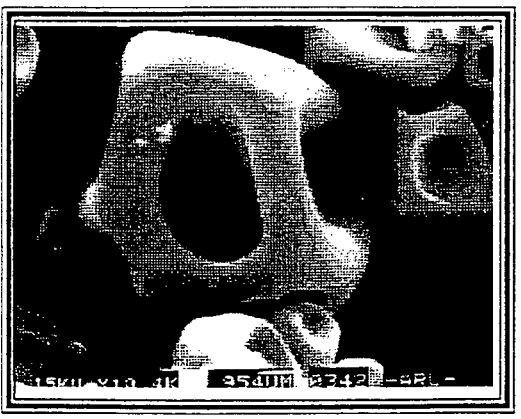

FIGS. 5 and 6 illustrate SEM image examples of silica doughnut-shaped particles that are coated with zirconium silicate spicules. Mean size being about 5 μm with a few larger particles being about 15 μm.

FIG. 7 to 12 illustrate SEM image examples of multi-dimpled shaped ceramic particles of zirconium silicate according to the present invention with mean particle size of about 6 to 7 μm.

Figure 13:
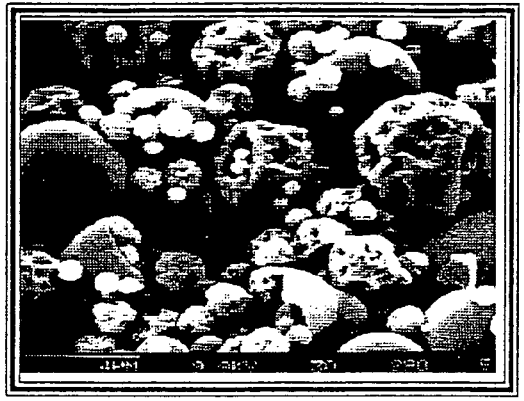

FIG. 13 illustrates SEM image examples of multi-dimpled and spherical shaped mullite ceramic particles. Mean particle size of about 2 μm.

Figure 14:
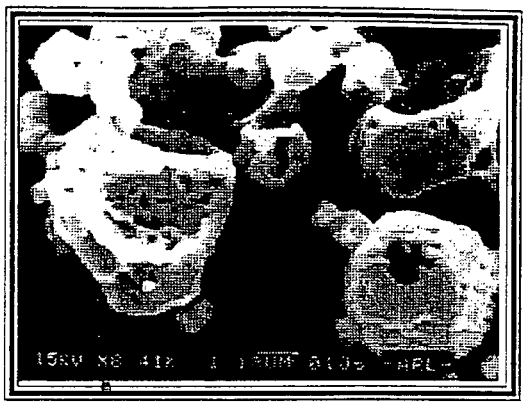

FIG. 14 illustrates a SEM image example of barium silicate porous multi-dimpled shaped particles ranging from 0.5 to 5 μm.

Figure 15:
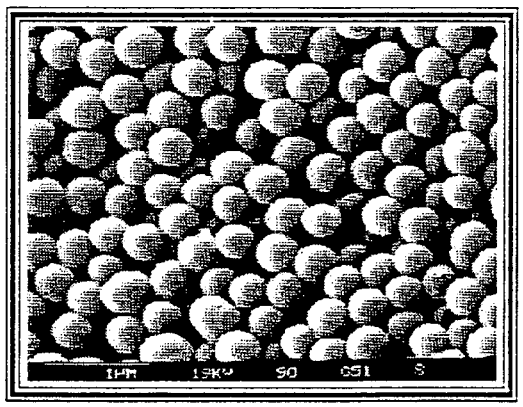

FIG. 15 is a SEM illustrating examples of mono-sized silica spherical particles with a size of about 0.3 μm.

Figure 16:
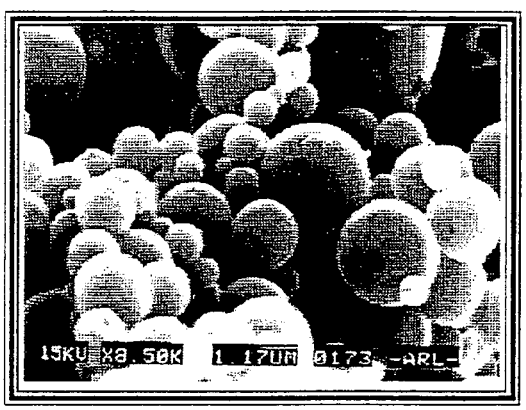

FIG. 16 is a SEM impage illustrating examples of zirconium silicate spherical particles.

Figure 17:
Figure 18:
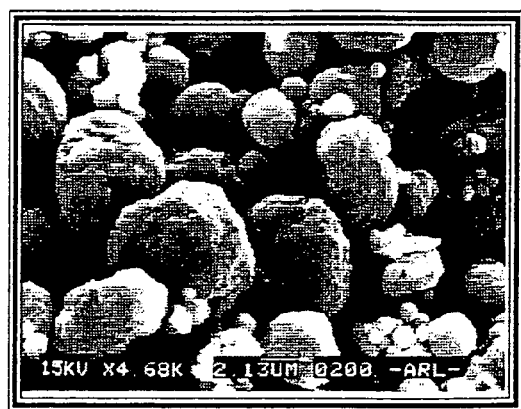

FIGS. 17 and 18 illustrate SEM image examples of nugget shaped particles of strontium and barium silicates.

Figure 19:
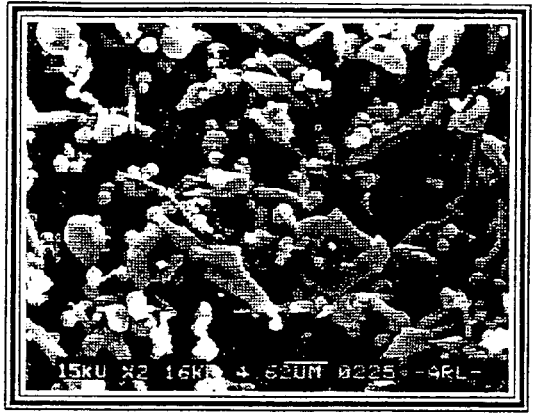
Figure 20:
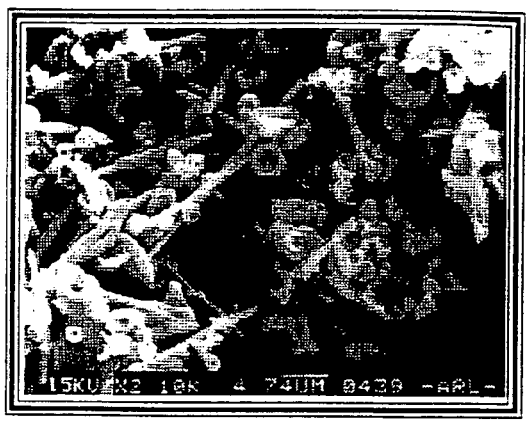

FIGS. 19 and 20 illustrate SEM image examples of zirconium silicate rod and fiber-shaped particles.

Figure 21:
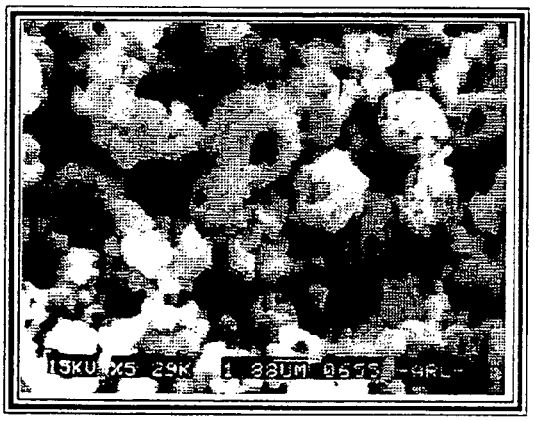
Figure 22:
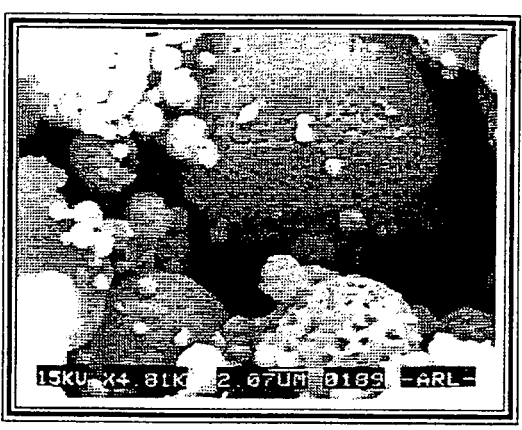
Figure 23:
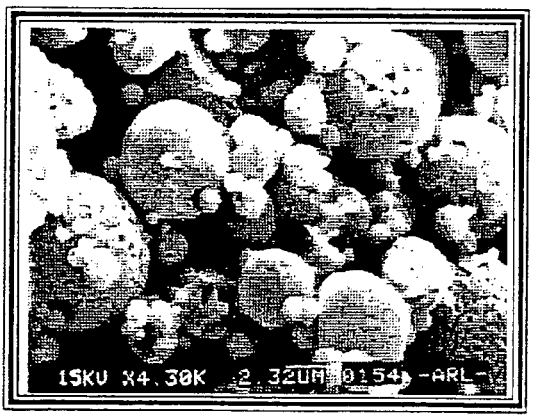
Figure 24:
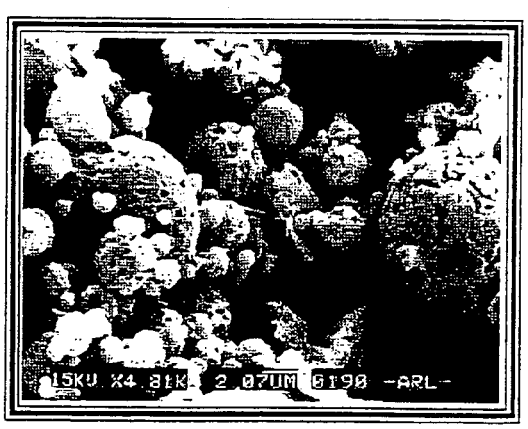
Figure 25:
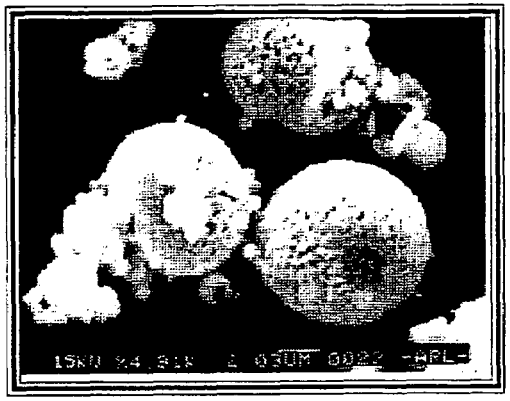
Figure 26:
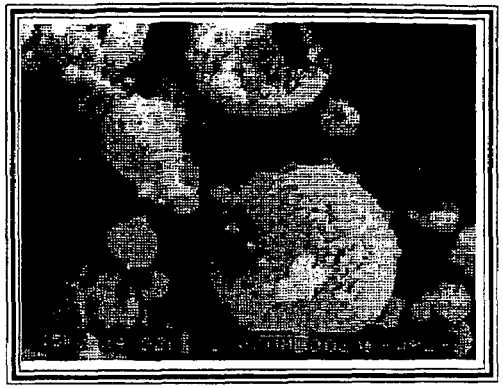
Figure 27:
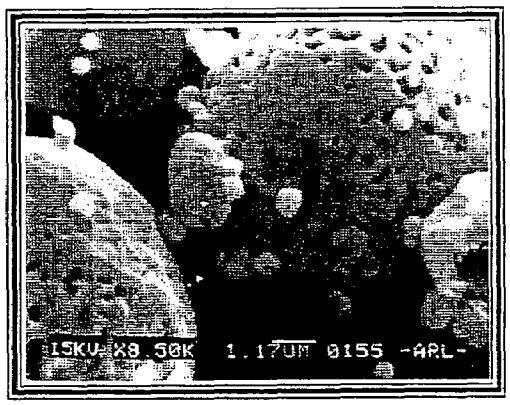
Figure 28:
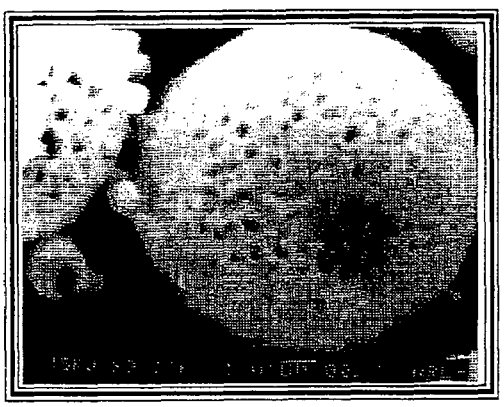
Figure 29:
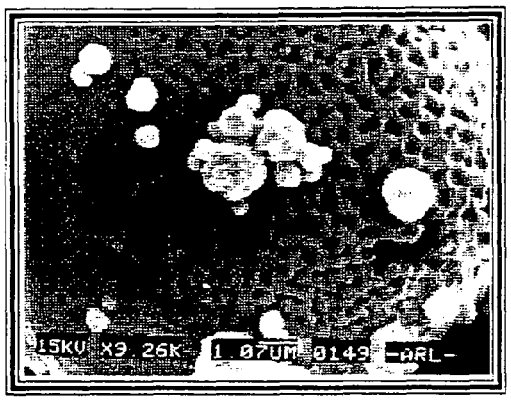

FIG. 21 illustrates a SEM image example of hollow semi-spherical crystalline robust heavy plate-like shaped particles of barium silicate.

FIGS. 22 to 29 illustrate SEM image examples of barium silicate hollow spherical shaped particles with a delicate porous mesh surface.

Figure 30:

FIG. 30 illustrates a SEM image example of barium silicate hollow spherical porous "ball of wool-like" particles.

The above characteristic shapes can be consistently reproduced, the size and chemical composition can be varied by changing the conditions of synthesis.

The above shapes can be produced with various chemical compositions.

PREFERRED EMBODIMENT FOR CARRYING OUT THE INVENTION

The present invention provides a method for producing discrete unique ceramic particles having specific size, shape, topography and chemistry. These particles can be used as the reinforcing phase in a resin matrix composite for use as a dental filling material and other non-dental applications. Some particles will require to possess the property of radiopacity, to allow diagnostic X-ray images to be produced of fillings in teeth to permit an assessment of the presence of any further dental decay adjacent to the filling. The ceramic particles are specifically designed to function as a reinforcing strengthening phase in a resin/ceramic composite material. These particles represent a unique and novel approach to the production of ceramic filler particles for dental composite biomaterials. The ceramic particles will possess unique shape and texture characteristics not previously in existence for dental composite filling materials. The ceramic particles will lead to the technological development of significantly improved dental composite materials with enhanced fracture toughness and wear resistance.

This invention concerns an aqueous acid solution or suspension of precursors for producing glass, glass-ceramic or ceramic particulate materials. The aqueous acid solution or suspension of the invention comprises a combination of all the precursors necessary to give a finished product when the precursor composition is dried and fired. This invention is not limited to any particular wet-chemical method of synthesis or any particular precursors for any specific glass, glass-ceramic or ceramic particulate materials. On the contrary, any combination of precursors or wet chemical synthesis methods can be employed which will result in unique shaped particles for use as a reinforcing phase in a ceramic or glass-ceramic or ceramic/resin composite.

At least six basic wet chemical synthesis methods may be used to produce ceramic or glass filler particles, the term "wet-chemical synthesis" means any of the following six methods: 1) sol-gel polymerization of prehydrolyzed alkoxides (some soluble metal salts may be added becoming complexed into the gel). 2) The precipitation of precursors from suspensions by spray-drying, spray-freeze drying or freeze-drying. 3) Room temperature or elevated aqueous solution precipitation synthesis methods. 4) Hydrothermal synthesis in which the aqueous solutions or suspensions of precursor materials are heated at elevated temperatures and pressures. 5) Organic solution synthesis precipitation methods, and 6) Glycothermal synthesis in which the organic solutions or suspensions of precursor materials are heated at elevated temperatures and pressures. These methods allow homogeneous glasses, ceramics and glass-ceramics to be formed at temperatures well below the normal temperature required to sinter high density bodies of uniform microstructure. The unique shapes are achieved by careful control of the parameters such as: chemistry of starting solution, the viscosity and age of the solution, the concentration of the solution, the temperature used during the dehydration process, and the like. The term "shaped particles" means that the particles possess a distinct shape and topography which lends itself to aiding the mechanical locking of the resin matrix with the particle. For the sake of brevity the terms glass or ceramic are employed to refer to any combination of inorganic glass, ceramic or glass-ceramic structure. The term "aqueous solution" means an aqueous solution, suspension or dispersion which may be acidic, neutral or basic, which may contain a range of salts and polymeric substances. This invention also concerns specific shaped particles formed during dehydration of the aqueous solution and or during subsequent calcining of the glass precursor powder. This invention also concerns shaped particles of glass or ceramic made by spray-drying or other wet chemical method of synthesis in which the precursor aqueous solution is subsequently dehydrated and calcined producing a precursor powder.

The aqueous solutions of this invention preferably have a pH typically below about 5. Preferred acids for pH control are those that decompose cleanly on heating and leave no residue that would require prolonged calcination.

A variety of unique shaped filler particles are employed such as: doughnut, spherical, multi-dimpled, porous hollow spheres and nugget. The chemistry of these particles can be, alumina, mullite, silica, or silica compounds containing zirconium, strontium, barium, titanium, or combinations of similar elements and compounds. The appearance and size of the particles shown in the SEM images FIGS. 1 to 30 are for illustrative purposes only and are not intended to covey absolute limitations of the invention. In this regard, it is understood that each individual particle of a given shape can vary up to about 50 micrometers or larger. Preferred particles sizes will be provided below.

A major feature of this invention is the production of unique shaped ceramic particles which have a very reproducible controlled shape, particle size and distribution with no need for grinding or sieving. The silica, alumina, zirconium silicate, barium silicate, strontium silicate and mullite ceramic particles produced using wet chemistry possessing unique shapes for use as fillers in composite systems provide mechanical locking for the filler within the resin matrix. These customized shapes have the capability of preventing pull-out from the resin matrix during abrasion. Tests have been conducted which indicated that composite formulations containing unique shaped particles demonstrate excellent abrasion resistance and fracture toughness.

The following seven types of zirconium silicate particles have been produced with unique characteristic shapes.

1) Spherical (25% Zr oxide)
2) Spherical (15% Zr oxide)
3) Spherical (8% Zr oxide)
4) Multi dimple (25% Zr oxide)
5) Multi dimple (15% Zr oxide)
6) Mixture of spherical and multi dimple (8% Zr oxide)
7) Mixture of spherical and multi dimple (4% Zr oxide)
8) Doughnut (4% Zr oxide)
9) Rods or fibre (25% Zr oxide)
10) Rods or fibre (35% Zr oxide)

Examples of typical mean particle size and the mean size of the 10 and 90 percentiles are shown in Table 1. The particle size and distribution is extremely reproducible and can also be varied within a limited range by changes in parameters of flow rate and concentration of solution or suspension.

TABLE 1

Examples of typical mean particle size.

| Particle Type | Mean μm | 10% Mean μm | 90% Mean μm |
|---|---|---|---|
| 1 spherical | 7.69 | 1.93 | 14.14 |
| 4 Multidimple | 7.77 | 2.08 | 14.14 |
| 5 Multidimple | 6.1 | 1.84 | 11.00 |
| 6 Mixture | 4.63 | 1.3 | 9.13 |
| 7 Mixture | 5.34 | 1.32 | 10.82 |
| 8 Doughnut | 5.14 | 1.80 | 8.81 |
| 9 Rods | Length 15-25 μm Diam. 0.3-4 μm | | |

The three major variables affecting the shape of particles are the time of the reaction or the age of the solution, the pH and the actual chemistry of the solution. The longer time or older solutions give the unique multi-dimple shapes, while the shorter times give spherical particles. The much longer time or much older solutions containing the higher percentage of zirconium produce particles which include the rod or fibres.

The barium silicate particles containing 70, 60, and 40% and 4% BaO and strontium silicate containing 4% SrO exhibit the following nine types of particle shapes.

1) 70% BaO—Hollow semi-spherical cyrstalline heavy robust plate-like structure, mean particle size 1-3 μm (FIG. 21).
2) 60% BaO—Hollow spherical delicate mesh structure, mean particle size 2-5 μm (FIGS. 22 to 29).
3) 60% BaO—Hollow spherical delicate mesh structure combined with multi-dimple shapes, mean particle size 2-5 μm.
4) 40% BaO—Mixture of non-porous spherical multi-dimple and doughnut shapes, mean particle size 2-5 μm.
5) 40% BaO—Mixture of porous spherical multi-dimple and some doughnut shapes, mean particle size 3-6 μm.
6) 4% BaO non-porous spherical particles, typically 1 to 10 μm, with a mean size of about 4 μm.
7) 4% BaO 'Nugget Shaped' particles typically 1 to 10 μm, with a mean size of about 4 μm (FIG. 18).
8) 4% SrO non-porous spherical particles typically 1 to 10 μm, with a mean size of about 4 μm.
9) 4% SrO 'Nugget Shaped' particles, typically 1 to 10 μm, with a mean size of about 4 μm (FIG. 17).

The first of the barium silicate shapes is best described as a spherical mesh-like structure built up from what looks like crystalline plate-like structures. The second is a general spherical shape possessing a porous surface and a third exhibits a delicate mesh structure combined with some multi-dimple shapes. The fourth versions comprise a mixture of non-porous spherical particles together with doughnut, and multi-dimple shapes. The fifth version of the barium silicate (40% BaO) particles differs from the fourth type in that the spherical shapes exhibit porosity. Tests have confirmed the consistency and reproducibility of synthesizing the shape and texture for these particles. These barium silicate particles provide a structure for the polymerizable resin to penetrate and mechanically lock into. X-ray analysis has confirmed the crystalline nature of the first type of unique barium silicate particles. Adequate radio-opacity is considered to be mandatory for posterior dental composite materials in facilitating the diagnosis of secondary caries adjacent to the restoration. Translucency is not particularly important for posterior restorations, from the point of view of aesthetics; however, for curing systems it is important to achieve an adequate depth of cure. Thus, translucency has to be balanced with the need to have adequate radio-opacity.

Surface area: The multi-dimpled zirconium particles have a surface area in the range of 2-3 $m^2/g$, which is greater than two of the spherical shaped (non-dimpled) particles of zirconium silicate. The combination of multi-dimple and rod like particles gave a significantly higher surface area of 18.06 $m^2/g$. the different forms of the barium silicate particles have surface areas ranging from 3.10 to 4.37 $m^2$ g, which is generally greater than for the zirconium silicate particles, the exception being the combination of multi-dimple and rod like zirconium silicate particles.

TABLE 2

| Surface area $m^2/g$ for Ceramic particles | |
|---|---|
| Silica doughnut | 66.6 ± 0.7 |
| Mono sixed spherical silica | 9.66 ± 0.1 |
| Barium Oxide-Silica: | |
| Hollow Spherical Porous | 4.14 ± 0.09 |
| Hollow Spherical Porous Mesh | 3.11 ± 0.18 |
| Zirconium Silicate: | |
| Doughnuts (4% $ZrO_2$) | 2.61 ± 0.09 |
| Multi-dimpled (15% $Zr_O2$) | 2.11 ± 0.01 |
| Multi-dimpled and Rods (25% $ZrO_2$) | 18.06 ± 0.53 |
| Multi-dimpled (25% $ZrO_2$) | 3.04 ± 0.10 |
| Spherical and Multi-dimpled (25% $ZrO_2$) | 3.18 ± 0.04 |
| Spherical | 1.89 ± 0.12 |

The examples of the various surface areas exhibited by the different forms of particles of this invention shown in Table 2 allow for the blending of different particles to optimize the desired consistency when mixed with the polymer resin.

Modulus of elasticity tests have confirmed that the customized silica, alumina, mullite, zirconium silicate, barium silicate strontium and titanium silicate ceramic particles produced by wet chemistry synthesis possessing unique shapes for use as a fillers in composite systems provide mechanical locking for the filler within the resin matrix.

These shapes have shown that they provide improved mechanical performance for a resin/glass or ceramic composite systems. The customized shapes should prevent pull-out from the resin matrix during abrasion.

Excessive elastic deformation of the restorative material under functional stress may result in catastrophic fracture of surrounding brittle tooth enamel structure, or alternatively increased micro-leakage may result. However, it is the property of fracture toughness which is the most important mechanical property. Currently dental composite an dental amalgam restorative materials have fracture toughness $K_{IC}$ values well below 2 MPa·m$^{1/2}$. The incorporation of 20% of the unique shaped ceramic barium silicate filler of this invention into a composite formulation has produced fracture toughness $K_{IC}$ values of over 3 MPa·m$^{1/2}$. Fracture toughness values for 10 commercial dental composite materials together with an experimental formulation containing 20% of the unique shaped barium silicate hollow porous spheres are illustrated in Table 3 below.

TABLE 3

Fracture Toughness of composite Materials

| Materials | Fracture Toughness ($K_{IC}$) MPa.m$^{1/2}$ |
|---|---|
| Charisma F | 1.18 ± 0.35 |
| Herculite XR Unidose | 1.26 ± 0.38 |
| Herculite XRV | 1.66 ± 0.32 |
| P-50 | 0.76 ± 0.08 |
| Silux Plus | 0.85 ± 0.11 |
| Solitaire | 0.72 ± 0.26 |
| Surefil | 1.56 ± 0.23 |
| Tetric Ceram | 1.37 ± 0.36 |
| TPH | 1.89 ± 0.18 |
| Z-100 | 1.11 ± 0.17 |

Experimental composite containing 20% (wt) barium silicate 'Hollow Porous Mesh Spheres' gave $K_{IC}$ values in excess of 3 MPa·m$^{1/2}$.

Current dental composites cannot withstand the aggressive environment of the oral cavity. Improved dental composite restoratives with significantly improved fracture toughness values and increased resistance to wear and abrasion are now possibly due to the development of the unique shaped filler particles of this invention.

Specifically 5-35% of the unique shaped filler paticles of this invention blened with conventional ground glass filler particles can provide vastly improved fracture toughness, excellent radio opacity (of at least 3 mm equivalent aluminium), as well as significantly imrpoving the resistance to wear.

Some dental composites are marketed as possessing a high packability force which simulates the handling characteristics of ental amalgam during placement. Other dental composite materials are marketed as flowable materials. A consistency test which evaluates the packability force has been used to compare five commercial composite materials with the experimental shaped particles (62 and 68% wt filler loading). As illustrated in the table below the Surefil (DENTSPLY) material exhibited the hightest value for any of the commercial materials but was only one third of the value for the experimental doughnut shaped material. The consistency can be influenced by the volume, shaped-size (surface area), and size distribution of the filler particles incorporated. The two experimental shaped ceramic particles, doughnut (109 N) and mono-sized spheres (4.6 N) of this invention can be used to blend with other ceramic particles in order to control the consistency desired.

TABLE 4

Packability Force for Composite Materials

| Materials | Packability Force (Newtons) |
|---|---|
| Exp. Doughnut shape (62% wt) | 109.00 ± 17.9 |
| Exp. Mono-sized spherical shape (68% wt) | 4.60 ± 0.26 |
| Surefil | 31.29 ± 1.64 |
| Herculite XR Unidose | 26.70 ± 2.67 |
| Solitaire | 23.26 ± 2.80 |
| Tetric Ceram | 20.36 ± 1.24 |
| TPH Compules | 10.78 ± 1.26 |

The unique-shaped ceramic particle produced in the form of a multi-dimpled zirconium, barium and strontium silicate which provides mechanical locking for the resin matrix, also provides appropriate radiopacity.

Figure 1:
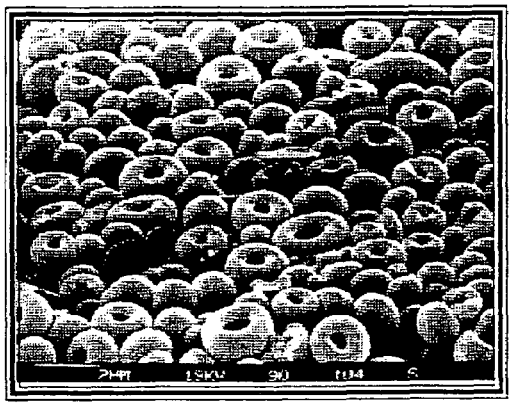
FIG. 1 is a SEM image example of doughnut-shaped silica ceramic particles according to the present invention. Mean size being about 5 µm with a few larger particles being about 15 µm.
Figure 2:
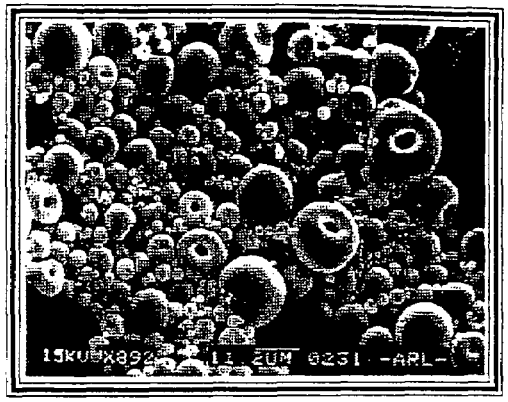
FIG. 2 is a SEM image example of doughnut-shaped zirconium silicate ceramic particles. Mean size being about 5 μm.
Figure 3:
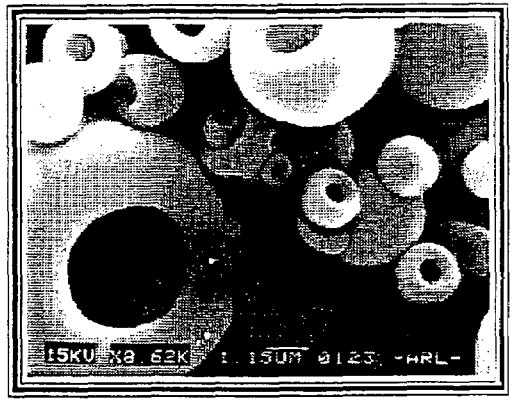
FIG. 3 illustrates a SEM image example of alumina doughnut-shaped particles, which have mean size of about 5 μm.
Figure 4:
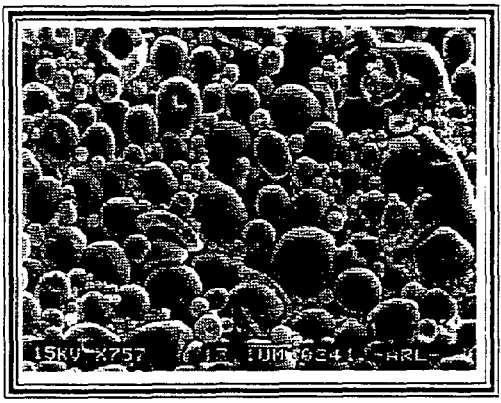
FIG. 4 illustrates a SEM image example of a mixture of alumina spherical and doughnut-shaped particles with a similar size and distribution.

To illustrate the production of the ceramic particles of this invention the following example is given. The filler particles are produced as either ovoid or round discs with a depression or hole through the centre (doughnut-shaped) at least about seventy five percent of the particles produced will have a hole (FIG. 1). The external size of these shapes ranges from about 0.2 up to about 20 μm, with a mean size of about 5 μm and they are chemically composed Of $SiO_2$. However, a small percentages of other ions such as Na and K may be incorporated (0.5 to 2%) in order to reduce the hardness. Barium, strontium, lanthanide, samarium, dysprosium, or terbium oxides may also be incorporated or coated onto the surface in order to produce a composition which will produce X-ray opacity. The particles are synthesized from a silicate suspension (concentration 10-40 wt % SiO2) which may also contain the additional elements if required. The method involves pumping the solution under pressure (of about 70 p.s.i.) through a nozzle (of about 0.5-0.7 mm diam.) at a flow rate of about 10 cc per minute into a chamber which is held at a temperature of about 200° C. The small droplets of solution are rapidly heated such that the vapour is eliminated from the external surface of the droplet with a small amount located internally due to the poor thermal conductivity of the silica particle. The final quantity of moisture from the centre of the particle is eliminated causing a hole to be produced in the particle. Final heating (at about 110-120° C.) in a second chamber with a partial vacuum of about 10 p.s.i. consolidates the hollow disc shape.

The flow rate for the solution and the nozzle and the chamber temperatures as well as the concentration of the solution or suspension are important to the formation of the desired particle shape and size. A further stage follows in which the particles are heated in a crucible in a furnace for about 24 hours at a temperature of about 600° C. This completes the conversion of the "silica gel" into "silica glass", and also completes in some cases the formation of the holes in the discs. The smooth ovoid or round doughnut ring-shaped particles or discs provide a lower residual stress within the matrix resin following polymerization than would be the case with conventional irregular shaped filler particles.

This invention provides a method for producing discrete unique ceramic particles having specific size, shape and chemistry. These particles will be used as the reinforcing phase in a resin-matrix composite for use as a dental filling material. Any resin material suitable for use in the oral cavity is within the scope of the invention. For example, those resins described in U.S. Pat. Nos. 4,514,174; 5,338,773 and 5,710,194 are useful. Those patents are hereby incorporated by reference for such disclosure.

Similar doughnut shaped particles can also be made from alumina (aqueous suspension of $Al_2O_3$) and these can be used in resin matrix composites or be incorporated into a glass to produce an alumina/glass composite system of enhanced strength for use as a biomaterial to replace natural hard tissues.

The various unique-shaped ceramic particles can be synthesized for incorporation into various cements of the carboxylate or phosphate type.

Further, the various composite and cement systems mentioned can have special application in a wide range of varied commercial and industrial uses outside the field of dental and medical use.

The surface of the ceramic particles is preferably coated with a silane coupling agent such as 3-(Methacryloxypropyl)-trimethoxysilane. This will be achieved by the particles in a solution of the silane compound and subjecting it to a drying process. The particles may also be treated with a plasma cleaner in order to aid the wetting of the silicate with the organic monomers. Plasma cleaning, involves exposing the surface of the substrate to a gas discharge, which provides a gentle yet thorough scrubbing of the surface removing contaminants and increasing the surface energy may be used.

The sub micron sized spherical filler particles are produced by precipitation from a silica or alumina alkoxide solution by pH control. These smaller particles may be blended together with the unique shaped particles together with conventional glass filler in varying proportions in order to produce a desired packing density, of 75 to 80% by weight of the total filler. The colour and opacity produced with this composite system in the absence of any shading pigments has been found to resemble closely that of natural teeth, and to be close to typical commercial dental composite basic universal shades. The system can thus very easily be modified by incorporation of shading pigments according to the known art to product additional shades which may be required. The special unique-shaped particles may also be blended together (5 to 35 wt %) with finely divided inorganic material such as a barium aluminosilicate glass or other glass having an effective amount of radiopaque oxide that renders the resultant glass radiopaque to X-rays according to the known dental art such as in U.S. Pat. No. 3,911,581 which is incorporated by reference.

The unique shaped ceramic particles (5 to 35 wt %) are then blended with conventional glass filler under vacuum, or any other suitable method, with a resin system such as bis phenol dimethacrylate, BIS-GMA, TEGDMA, propyl methacrylate-urethane or diethylene glycol dimethacrylate, or hexamethylene diisocyanate adduct of the diglycidyl methacrylate adduct of bisphenol A, according to, for example, U.S. Pat. No. 3,629,187 which is incorporated by reference for such disclosure. The photo-curing composite material will use camphoroquinone or similar system in order to produce polymerization.

Tests have been conducted in order to evaluate the elastic moduli and Poisson's ratio for the experimental composite systems of the above type. The purpose of these tests were to determine the influence of type and volume of ceramic fillers on the dynamic moduli of elasticity and Poisson's ratio for the experimental composite materials. Considerations of the fundamental property of modulus of elasticity and fracture toughness for the matrix resin, as well as for blends of the various unique filler with different matrix combinations together with the influence of silanization have been used to optimize the composite systems. Studies of the moduli of elasticity and fracture toughness of experimental composite materials have been able to indicate the effectiveness of the stress/strain transfer from the matrix to the filler particles. Materials with a higher modulus of elasticity and fracture toughness are required for restorations placed in back (molar) teeth. The effectiveness of mechanical locking of ceramic particles into the resin matrix was evaluated using an ultrasonic method. Experimental composite formulations were evaluated in which the ceramic filler types were synthesized by wet chemistry in which some particles were spherical (essentially mono size 0.3-0.4 µm) and others were non-spherical, non-angular, smooth-surface particles of doughnut shape (particle size 1.0-8.0 µm, average particle size of 5.0 µm). The surface areas for both filler types were respectively, 9.66 ($m^2/g$) and 66.58 ($m^2/g$). Tests with no silane treatment of ceramic filler particles were undertaken and compared with silane treated filler in order to allow study of the influence of the size and shape of filler particle in terms of mechanical locking alone. The filler loading was also varied. Significant effects were established for mechanical locking and silane treatment and the contribution of the ceramic filler to the elastic modulus.

The matrix resins to be used with the unique-shaped particles of this invention can be mixtures of BIS-GMA and TEGDMA, or urethane dimethacrylates and large oligomeric structures of BIS-GMA-urethanes may also be used. Combinations of these materials and the like may be employed. The materials of this invention will have a blend of the unique shaped glass, glass-ceramic or ceramic particles combined with conventional glass filler if desired dispersed in a polymerizable synthetic organic resin matrix. The monomer materials being blended together with the inorganic (filler) reinforcing phase such as a mullite, alumina, calcium aluminosilicate, zirconium silicate, barium silicate, titanium silicate or strontium aluminosilicate glass, glass-ceramic or ceramic unique-shaped particles. Preferably blending of large and small particles (distribution, from 0.04 to 10 µm) should be used to obtain optimum packing density and mechanical properties. However, a small proportion of some particles in the range 10 to 50 µm can also be incorporated to improve translucency and other physical properties. Various blends of particle size and shape can be used to achieve maximum loading density. The size and distribution of the filler particles and the refractive index of filler and matrix resin should be optimized to give appropriate translucence for natural aesthetic results. The filler particles of such composites should preferably be surface treated to provide adhesion between the resin matrix and the glass or ceramic filler particles. Adhesion being achieved by using a silane (organo functional adhesion promoter) treatment. The composite systems of this invention may also contain 2-25% (preferably 5-10%) of fumed silica to adjust viscosity and handling characteristics. This sub-micron silica also being treated with a silane coupling agent to reduce the uptake of water by the large surface area. Such composite materials may use photo-polymerizing systems activated by visible light in which a light sensitive absorber such as camphorquinone is used together with an aliphatic amine accelerator. However, chemically activated composite systems using the N,N-dimethyl-para-toluidine and benzoyl peroxide or similar system for chemical activation may also be appropriate, as will the heat curing systems since the composite systems using the unique filler may also have application in the from of indirect dental restorative devices such as inlay or onlays fabricated outside the mouth. Unless otherwise stated, all "percents", % and the like are weight percents.

What is claimed is:

1. A filled dental material having improved mechanical properties comprising:
   a resin matrix and a filler component;
   wherein said filler component comprises from about 5 to about 35 percent by weight of ceramic particles having a first preselected shape; said first preselected shape selected from the group consisting of doughnuts, multi-dimples, porous hollow spheres, nuggets, and mixtures thereof; and
   wherein said filler component further comprises ceramic particle having a second preselected shape selected from the group consisting of rods, fibers, spheres and mixtures thereof;
   wherein the filled dental material is improved due to mechanical interlocking of the ceramic particles within the matrix.

2. A filled dental material as in claim 1, wherein said filler component comprises multi-dimpled shaped particles and wherein said particles are porous.

3. A filled dental material as in claim 1, wherein said filler component comprises multi-dimpled shaped particles and wherein said particles are solid.

4. A filler material for a dental restorative composition comprising:
   a plurality of ceramic particles having a preselected mixture of doughnut and sphere shapes.

5. A filler material as in claim 4, wherein said filler is produced by wet chemical synthesis of a material selected from the group consisting of zirconium, silica, barium, titanium, strontium, alumina, mullite or mixtures thereof.

6. A filler as in claim 5, wherein said filler is a mixture of silica and from about 3 to about 40 percent by weight of $ZrO_2$.

7. A filler as in claim 5, wherein said filler is a mixture of silica and from about 10 to about 80 percent by weight of BaO.

8. A filler as in claim 5, wherein said filler is a mixture of silica and from about 3 to about 40 percent by weight of $TiO_2$.

9. A filler as in claim 5, wherein said filler is a mixture of silica and from about 10 to about 80 percent by weight of SrO.

10. A filler as in claim 4, wherein said particles having a preselected shape have a mean diameter of less than 15 microns.

11. A filler as in claim 4, wherein said particles having a preselected shape have a mean diameter less than 10 microns.

12. A filler as in claim 4, wherein said particles having a preselected shape have a mean diameter of 5 microns.

13. A filled dental material having improved mechanical properties comprising:
    a resin matrix and a filler component;
    wherein said filler component comprises from about 5 to about 35 percent by weight of ceramic particles comprising porous multi-dimpled shaped particles;
    wherein the filled dental material is improved due to mechanical interlocking of the ceramic particles within the matrix.

14. A filled dental material having improved mechanical properties comprising:
    a resin matrix and a filler component;
    wherein said filler component comprises from about 5 to about 35 percent by weight of ceramic particles comprising solid multi-dimpled shaped particles;
    wherein the filled dental material is improved due to mechanical interlocking of the ceramic particles within the matrix.

15. A filled dental material as in claim 1, wherein the first preselected shape includes doughnuts.

16. A filled dental material as in claim 1, wherein the first preselected shape includes porous hollow spheres. wherein said porous hollow spheres are porous hollow mesh spheres.

17. A filled dental material as in claim 1, wherein the first preselected shape includes nuggets.

* * * * *